United States Patent
Turunen et al.

(10) Patent No.: US 11,230,691 B2
(45) Date of Patent: Jan. 25, 2022

(54) METHOD AND AN APPARATUS FOR AN ENZYMATIC HYDROLYSIS, A LIQUID FRACTION AND A LIGNIN FRACTION

(71) Applicant: UPM-KYMMENE CORPORATION, Helsinki (FI)

(72) Inventors: Sami Turunen, Lappeenranta (FI); Mauno Miettinen, Lappeenranta (FI); Meri Ventola, Lappeenranta (FI); Juha Tamper, Levänen (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 15 days.

(21) Appl. No.: 16/340,481

(22) PCT Filed: Oct. 12, 2017

(86) PCT No.: PCT/FI2017/050714
§ 371 (c)(1),
(2) Date: Apr. 9, 2019

(87) PCT Pub. No.: WO2018/069575
PCT Pub. Date: Apr. 19, 2018

(65) Prior Publication Data
US 2019/0241862 A1    Aug. 8, 2019

(30) Foreign Application Priority Data
Oct. 13, 2016 (FI) .................................. 20165782

(51) Int. Cl.
*C12P 19/00*    (2006.01)
*C12M 1/00*    (2006.01)
(Continued)

(52) U.S. Cl.
CPC ................ *C12M 45/06* (2013.01); *B01D 1/02* (2013.01); *C08H 6/00* (2013.01); *C12M 45/09* (2013.01);
(Continued)

(58) Field of Classification Search
CPC .......... C12P 19/00; C12P 19/02; C12P 19/14; Y02E 50/10
See application file for complete search history.

(56) References Cited

U.S. PATENT DOCUMENTS 7,354,743 B2    4/2008    Vlasenko et al.

FOREIGN PATENT DOCUMENTS

| CN | 104846033 A | 8/2015 |
| EP | 2548965 A1 | 1/2013 |

(Continued)

OTHER PUBLICATIONS

Helle et al., Biotech. Bioenginner., 1993, 42: 611-617. (Year: 1993).*

(Continued)

*Primary Examiner* — Allison M Fox
*Assistant Examiner* — Qing Xu
(74) *Attorney, Agent, or Firm* — Nixon Peabody LLP (57) ABSTRACT

A method and apparatus for enzymatic hydrolysis where a plant based feed is hydrolysed using an enzyme to form a hydrolysed product. An additive for preventing enzyme adsorption is fed to an enzymatic hydrolysis stage, the plant based feed, the hydrolysed product, a starting material, and/or a plant based material formed from the starting material. The hydrolysed product is supplied from the enzymatic hydrolysis stage to a first solid-liquid separation stage where a lignin fraction comprising the additive and a liquid composition comprising the enzyme are separated. The liquid composition is mixed with the plant based material in (Continued)

a mixing stage, forming a mixture. A solid and liquid fraction are separated from the mixture in a second solid-liquid separation stage. At least part of the solid fraction comprising the enzyme is fed as the plant based feed to the enzymatic hydrolysis stage.

15 Claims, 3 Drawing Sheets

(51) Int. Cl.
*C08H 7/00* (2011.01)
*C12P 19/02* (2006.01)
*B01D 1/02* (2006.01)
*C12P 19/14* (2006.01)

(52) U.S. Cl.
CPC ............... *C12P 19/00* (2013.01); *C12P 19/02* (2013.01); *C12P 19/14* (2013.01); *Y02E 50/10* (2013.01)

(56) References Cited

FOREIGN PATENT DOCUMENTS

| WO | 2007147263 A1 | 12/2007 |
| WO | 2008134037 A1 | 11/2008 |
| WO | 2015104459 A1 | 7/2015 |
| WO | 2016161515 A1 | 10/2016 |

OTHER PUBLICATIONS

Tu M. et al. Recycling cellulases during the hydrolysis of steam exploded and ethanol pretreated lodgepole pine. Biotechnology Progress, 2007. vol. 23, No. 5, p. 1130-1137.
Tu M. et al. The potential of enzyme recycling during the hydrolysis of a mixed softwood feedstock. Bioresource Technology, 2009. vol. 100, No. 24, p. 6407-6415.
Mesa L. et al. An approach to cellulase recovery from enzymatic hydrolysis of pretreated sugarcane bagasse with high lignin content. Biocatalysis and Biotransformation, 2015. vol. 33, No. 5-6, p. 287-297.
Search Report from Patent Application No. 20165782 dated May 12, 2017.
International Search Report from International Application No. PCT/FI2017/050714 dated Dec. 19, 2017.
Saini Jitendra Kumar et al., "Cellulase adsorption on lignin: A roadblock for economic hydrolysis of biomass", Renewable Energy, vol. 98, Apr. 4, 2016.

\* cited by examiner

METHOD AND AN APPARATUS FOR AN ENZYMATIC HYDROLYSIS, A LIQUID FRACTION AND A LIGNIN FRACTION

CROSS-REFERENCE TO RELATED APPLICATIONS

This application is a U.S. National Stage of International Application No. PCT/FI2017/050714, filed Oct. 12, 2017, which claims the benefit of Finish Patent Application No. 20165782, filed Oct. 13, 2016, both of which are hereby incorporated by reference in their entireties.

FIELD

The invention relates to a method and an apparatus for an enzymatic hydrolysis. Further, the invention relates to a liquid fraction and a lignin fraction and their use.

BACKGROUND

It is known different methods for forming carbohydrates and lignin from different raw materials, such as biomass. Many bio-refinery processes, e.g. hydrolysis, generate lignin and sugars after the treatment of the biomass. It is known to use an enzymatic hydrolysis in the bio-refinery processes.

OBJECTIVE

The objective of the invention is to improve an enzymatic hydrolysis. Another objective is to provide a new method for carrying out the enzymatic hydrolysis. Another objective is to produce a liquid fraction and a lignin fraction in connection with the enzymatic hydrolysis. Another objective is to decrease an enzyme dosage.

SUMMARY

The method for the enzymatic hydrolysis is characterized by what is presented in claim 1.
The apparatus for the enzymatic hydrolysis is characterized by what is presented in claim 17.
The lignin fraction is characterized by what is presented in claim 22.
The liquid fraction is characterized by what is presented in claim 23.
The use of the lignin fraction is characterized by what is presented in claim 24.
The use of the liquid fraction is characterized by what is presented in claim 25.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings.

DETAILED DESCRIPTION

In a method for an enzymatic hydrolysis plant based feed (1), preferably cellulose based material, is fed to an enzymatic hydrolysis stage (2) in which the plant based feed is hydrolysed by means of an enzyme (23,3) to form a hydrolysed product (5). In the method an additive (4) for preventing an enzyme adsorption is fed to the enzymatic hydrolysis stage (2), to the plant based feed (1) which is fed to the enzymatic hydrolysis stage (2), to the hydrolysed product (5), to a starting material (20) and/or to a plant based material (10) formed from the starting material (20), the hydrolysed product (5) is supplied from the enzymatic hydrolysis stage (2) to a first solid-liquid separation stage (6) in which a lignin fraction (7) comprising the additive (4) and a liquid composition (8) which comprises the enzyme are separated, the liquid composition (8) is mixed with the plant based material (10) in a mixing stage (9) after the separation stage (6) in order to form a mixture (11), a solid fraction (14) and liquid fraction (15) are separated from the mixture (11) in a second solid-liquid separation stage (13) after the mixing stage (9), and at least a part of the solid fraction (14) which comprises the enzyme is fed as the plant based feed (1) to the enzymatic hydrolysis stage (2).

Figure 1:
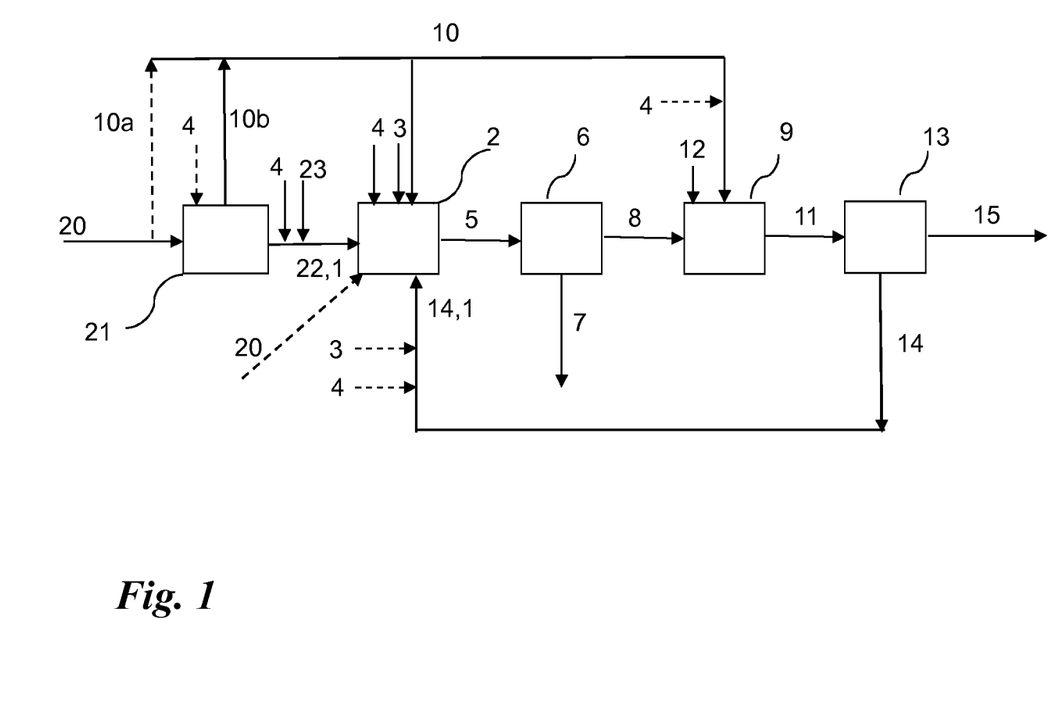
FIG. 1 is a flow chart illustration of a method according to one embodiment.
Figure 2:
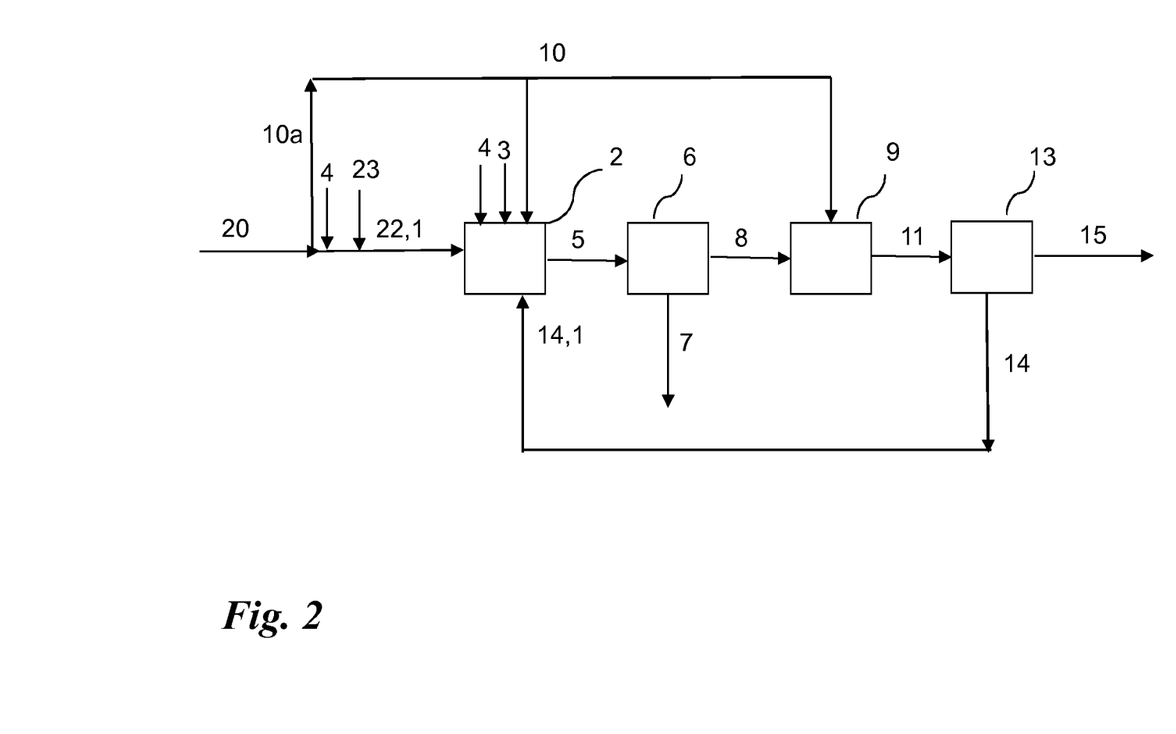
FIG. 2 is a flow chart illustration of a method according to another embodiment.

One embodiment of the method is shown in FIG. 1. Another embodiment of the method is shown in FIG. 2.

The apparatus comprises an enzymatic stage (2) and at least one feeding device for feeding a plant based feed (1) to the enzymatic hydrolysis stage (2) in which the plant based feed is hydrolysed by means of an enzyme (23,3) to form a hydrolysed product (5). The apparatus comprises at least one additive feeding device for feeding an additive (4) for preventing an enzyme adsorption to the enzymatic hydrolysis stage (2), to the plant based feed (1) which is fed to the enzymatic hydrolysis stage (2), to the hydrolysed product (5), to a starting material (20) and/or to a plant based material (10) formed from the starting material (20), at least one first solid-liquid separation stage (6) in which a lignin fraction (7) comprising the additive (4) and a liquid composition (8) which comprises the enzyme are separated from the hydrolysed product (5), at least one mixing stage (9) after the first solid-liquid separation stage (6) in which the liquid composition (8) is mixed with the plant based material (10) in order to form a mixture (11), at least one second solid-liquid separation stage (13) in which a solid fraction (14) and a liquid fraction (15) are separated from the mixture (11) after the mixing stage (9), and at least one recirculation device for feeding at least a part of the solid fraction (14) which comprises the enzyme as the plant based feed (1) to the enzymatic hydrolysis stage (2). Further, the apparatus may comprise at least one means for recovering the lignin fraction (7) and/or the liquid fraction (15) or for supplying the lignin fraction and/or the liquid fraction out from the apparatus or means for supplying the lignin fraction and/or the liquid fraction to the other treatment stage.

In this context, an enzymatic hydrolysis means any enzymatic hydrolysis. In one embodiment, the enzymatic hydrolysis is an enzymatic hydrolysis of carbohydrates, e.g. cellulose.

In this context, a liquid composition (8) means any liquid composition, which comprises mainly soluble carbohydrates and from which a solid lignin fraction has been separated. The liquid composition comprises enzyme. In a preferred embodiment, the liquid composition includes carbohydrates, preferably C6 carbohydrates ($C_6H_{12}O_6$ or $C_6(H_2O)_n$). Further, the liquid composition may include C5 carbohydrates ($C_5H_{10}O_5$ or $C_5(H_2O)_n$. The liquid composition may comprise carbohydrates, such as monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or ($C_5H_8O_4)_n$). In one embodiment, the liquid composition comprises soluble C5 and C6 carbohydrates and other carbohydrates. In one embodiment, the liquid composition comprises soluble C5 carbohydrates and other carbohydrates. In one embodiment, the liquid composition comprises soluble C6 carbohydrates and other carbohydrates. The liquid composition may comprise also other components.

In this context, a lignin fraction (7) means any lignin fraction comprising lignin, preferably lignin in solid form. The lignin fraction may be in the form of solids, e.g. solid cake, slurry, agglomerates or the like, when a liquid composition has been separated from the lignin fraction. However, some liquid or moisture is remaining in the lignin fraction. Further, the lignin fraction may comprise carbohydrates, e.g. solid C6 carbohydrates ($C_6H_{12}O_6$ or $C_6(H_2O)_n$). The lignin fraction may comprise also other carbohydrates and other components.

In this context, a hydrolysed product (5) is a product from an enzymatic hydrolysis stage (2). The hydrolysed product comprises a lignin fraction (7) and a liquid composition (8). The hydrolysed product (5) comprises lignin, carbohydrates and enzyme. The hydrolysed product is preferably in the form of a slurry or suspension.

In this context, a plant based feed (1) means any plant based feed which is fed to the enzymatic hydrolysis stage (2). In one embodiment, the plant based feed is formed from a starting material (20) which is a plant based starting material. In one embodiment, the plant based feed is the starting material (20). In one embodiment, the plant based feed is a treated starting material (10b, 22), e.g. from a pre-mixing stage (21). In one embodiment, the plant based feed is a mixture of the starting material, e.g. from a pre-mixing stage. In one embodiment, the plant based feed is formed from the starting material by treating the starting material. In one embodiment, the plant based feed is a solid fraction (14) from the second solid-liquid separation stage (13). In one embodiment, the plant based feed is a combination of the starting material (20), the treated starting material (10b) and/or the solid fraction (14).

In this context, a plant based material (10) means any plant based material which is formed from the starting material (20) and which is supplied to the mixing stage (9). In one embodiment, the plant based material (10) is the starting material (20). In one embodiment, the plant based material (10) is an untreated flow (10a) of the starting material (20). In one embodiment, the plant based material (10) is a treated flow (10b) of the starting material (20), e.g. from a pre-mixing stage. In one embodiment, the plant based material (10) is a mixture of the starting material, e.g. from a pre-mixing stage. In one embodiment, the plant based material (10) is formed from the starting material by treating the starting material.

In this context, starting material (20) means any plant based raw material, e.g. wood based raw material and/or other plant based material. Preferably, the starting material is cellulose based material. The starting material includes lignin, cellulose and hemicellulose. In one embodiment, the starting material is formed from material selected from the group consisting of wood based material, wood, lignocellulosic biomass, agricultural residues, bagasse based material, sugarcane bagasse, corn based material, corn stover, wheat straw, rice straw, woody biomass, woody perennials, vascular plants and the like and their mixtures and their combinations. In one embodiment, the starting material comprises wood based material or a mixture comprising wood based material. In one embodiment, the starting material is wood based material or a mixture comprising wood based material. In one embodiment, the wood based material is selected from hardwood, softwood or their combination. In one embodiment, the starting material comprises plant pieces, e.g. wood pieces. In one embodiment, the plant based feed (1) is wood based material or a mixture comprising wood based material In one embodiment, the starting material (20) comprises carbohydrates and lignin. Preferably, the carbohydrates have $C_n(H_2O)_n$ or $C_n(H_2O)_{n-1}$. The carbohydrates can comprise monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or ($C_5H_8O_4)_n$). Preferably, the starting material comprises carbohydrates, such as soluble carbohydrates, e.g. C5 carbohydrates ($C_5H_{10}O_5$ or $C_5(H_2O)_n$), and solid carbohydrates, e.g. C6 carbohydrates ($C_6H_{12}O_6$ or $C_6(H_2O)_n$).

The starting material (20) may contain one or more material components. In one embodiment, the starting material is in the form of suspension which contains liquid, such as water. Preferably, the starting material has been treated to dissolve at least part of hemicellulose. In one embodiment, the starting material (20) has been pre-treated, preferably by means of a suitable pretreatment. The pre-treatment stage may be selected from the group consisting of physical pretreatment, such as milling, extrusion, microwave pretreatment, ultra-sound pretreatment and freeze pretreatment, chemical pretreatment, such as acid pretreatment, alkaline pretreatment, ionic liquid pretreatment, organosolv pretreatment and ozonolysis, physico-chemical pretreatment, such as steam explosion pretreatment, ammonia fiber explosion pretreatment, $CO_2$ explosion pretreatment, liquid hot water pretreatment and wet oxidation, biological pretreatment and their combinations. In one embodiment, the starting material is treated by the hydrolysis, e.g. acid hydrolysis, autohydrolysis, thermal hydrolysis, supercritical hydrolysis and/or subcritical hydrolysis, in which at least a part of hemicellulose is separated from the raw material in connection with the hydrolysis. In one embodiment, the starting material is treated by the steam explosion, in which hemicelluloses are treated and in which at least a part of polysaccharides of the hemicelluloses convert into monosaccharides and oligosaccharides by means of a hydrolysis and in which pressure is rapidly released. In one embodiment, the starting material is treated by the hydrolysis and by the steam explosion in one or more steps. In one embodiment, the starting material is treated by the catalytic pretreatment, e.g. by using acid or base as catalyst. In the pretreatment stage the starting material enters the reactor unit where the pretreatment takes place. The starting material can be treated by means of one or more pretreatment. The treated starting material (20) can be then supplied directly or via an intermediate step or via an intermediate storage as a plant based feed (1) to the enzymatic hydrolysis stage (2). Further, in one embodiment, the starting material can be dewatered, e.g. by dewatering presses, and/or washed in one or two or more stages. The dewatering makes possible to separate sugar based streams.

In one embodiment, the plant based feed (1) is diluted with liquid, preferably with water, e.g. fresh water or recirculated process water e.g. from a lignin purification process, or steam condensate to form the feed to the enzymatic hydrolysis stage (2). In one embodiment, the plant based feed (1) is diluted with liquid in connection with the enzymatic hydrolysis stage (2) or before the enzymatic hydrolysis stage (2). Preferably, the plant based feed is diluted to suitable solid content. Dilution water may be added before the enzymatic hydrolysis stage or in a pre-mixing stage (21) or before the pre-mixing stage (21). In one embodiment, the plant based feed (1) is supplied without the dilution to the enzymatic hydrolysis stage (2). In one embodiment, dry matter of the plant based feed (1) is 2-60% by weight (TS, total solids, at 105° C.), preferably 4-40% by weight (TS, total solids at 105° C.), more preferable 10-30% by weight (TS, total solids, at 105° C.), in the enzymatic hydrolysis stage (2).

The plant based feed (1) is fed to the enzymatic hydrolysis stage (2). In one embodiment, the plant based feed (1) is fed to the enzymatic hydrolysis stage (2) as a uniform flow. In one embodiment, the plant based feed (1) is fed to the enzymatic hydrolysis stage (2) step by step or gradually for feeding material which have higher consistency than material in the enzymatic hydrolysis stage. In one embodiment, the plant based feed (1) is fed by means of any suitable feeding device, such as a pump, e.g. a mono pump or piston pump or other suitable pump, into the enzymatic hydrolysis stage (2). Selection of the feeding device is based on e.g. feed concentration and/or viscosity of the plant based feed. In one embodiment, the plant based feed (1) is hydrolysed in at least one enzymatic hydrolysis stage (2) with the enzymes. In one embodiment, the enzymatic hydrolysis stage is a continuous process stage. In one embodiment, the enzymatic hydrolysis stage is a batch process stage, e.g. a fed-batch process.

In one embodiment, the enzymatic hydrolysis stage (2) comprises at least one reactor, vessel, container, other suitable device or their combination in which the enzymatic hydrolysis is carried out. In one embodiment, the enzymatic hydrolysis stage (2) comprises at least one continuous enzymatic hydrolysis reactor. In one embodiment, the enzymatic hydrolysis stage (2) comprises at least one batch enzymatic hydrolysis reactor.

The enzymatic hydrolysis stage (2) may comprise one or more than one enzymatic hydrolysis step or one or more enzymatic hydrolysis reactor. In one embodiment, the enzymatic hydrolysis stage comprises one enzymatic hydrolysis step or one enzymatic hydrolysis reactor. In one embodiment, the enzymatic hydrolysis stage comprises more than one enzymatic hydrolysis steps or more than one enzymatic hydrolysis reactors. In one embodiment, the plant based feed (1) is hydrolysed in one or more than one enzymatic hydrolysis stages (2) with the enzymes. In one embodiment, the enzymatic hydrolysis stages or the enzymatic hydrolysis devices are arranged sequentially and/or in parallel. In one embodiment, the method and apparatus comprise more than one enzymatic hydrolysis stages or enzymatic hydrolysis devices which are arranged in parallel. When the enzymatic hydrolysis stages or enzymatic hydrolysis devices are arranged in parallel the enzymatic stage or devices can be processed at different rates and the process can be run continuously.

In one embodiment, an average residence time in the enzymatic hydrolysis stage (2) is below 100 hours, in one embodiment below 80 hours and in one embodiment below 72 hours. In one embodiment, the average residence time in the enzymatic hydrolysis stage is over 12 hours, in one embodiment over 24 hours, in one embodiment over 36 hours, and in one embodiment over 48 hours. In one embodiment, the average residence time in the enzymatic hydrolysis stage is between 12-100 hours, in one embodiment 24-80 hours, in one embodiment 36-76 hours and in one embodiment 48-72 hours. In one embodiment, a total residence time in the enzymatic hydrolysis stages (2) is below 100 hours, in one embodiment below 80 hours and in one embodiment below 72 hours. In one embodiment, the total residence time in the enzymatic hydrolysis stages is over 12 hours, in one embodiment over 24 hours, in one embodiment over 36 hours, and in one embodiment over 48 hours. In one embodiment, the total residence time in the enzymatic hydrolysis stages is between 12-100 hours, in one embodiment 24-80 hours, in one embodiment 36-76 hours and in one embodiment 48-72 hours.

In one embodiment, conversion level of cellulose is 60-100%, in on embodiment 70-95%, in one embodiment 75-90%, in the enzymatic hydrolysis.

The additive (4) for preventing an enzyme adsorption is fed to the enzymatic hydrolysis stage (2), to the plant based feed (1), to the hydrolysed product (5), to the starting material (20) and/or to the plant based material (10). The additive (4) may be fed at one or more than one feed point. In one embodiment, the additive (4) is fed to the enzymatic hydrolysis stage (2). In one embodiment, the additive (4) is fed to the plant based feed (1). In one embodiment, the additive (4) is fed to the hydrolysed product (5). In one embodiment, the additive (4) is fed to the starting material (20). In one embodiment, the additive (4) is fed to the plant based material (10) before the mixing stage (9) or in the mixing stage (9). In one embodiment, the material, e.g. the plant based feed (1), hydrolysed product (5), starting material (20) or plant based material (10), is mixed after the additive addition.

In this context, the additive (4) means any suitable additive which prevents an enzyme adsorption onto a predetermined surface, preferably onto lignin surface. In one embodiment, the additive (4) comprises at least one of a surfactant or polymer or their combination. In one embodiment, the additive (4) comprises at least one surfactant. In one embodiment, the additive (4) comprises one surfactant. In one embodiment, the additive (4) comprises more than one surfactant. In one embodiment, the additive (4) comprises at least one polymer. In one embodiment, the additive (4) comprises one polymer. In one embodiment, the additive (4) comprises more than one polymer. In one embodiment, the additive (4) comprises at least one surfactant and at least one polymer. The additive (4) may also comprise other components. The additive (4) may comprise one or more components. In one embodiment, the additive (4) comprises at least one surfactant and optionally at least another component. In one embodiment, the additive (4) comprises at least one surfactant and at least another component. In one embodiment, the additive (4) comprises at least one polymer and at least another component. In one embodiment, the additive (4) comprises a component which facilitates the function of the additive, e.g. the surfactant, and/or adsorption of the additive, e.g. the surfactant, on the lignin. In one embodiment, the additive (4) comprises a component which improves activity of the enzyme. Preferably, the additive (4) prevents the enzyme adsorption to solid lignin fraction (7) before, during or after the enzymatic hydrolysis stage (2). When the additive (4) is added before, during or after the enzymatic hydrolysis stage (2), the lignin surface is covered by the additive, e.g. by the surfactant, to prevent an enzyme adsorption on the lignin surface later in the process. In one embodiment, the surfactant or polymer is at least one of an amphiphilic compound, hydrophilic compound, non-ionic compound or anionic compound or their combination. In one embodiment, the surfactant or polymer is a hydrophilic, non-ionic compound. In one embodiment, the surfactant or polymer is selected from the group comprising polysorbate, polyoxyethylene, polyethylene glycol, sodium dodecyl sulphate, other suitable compound or their combinations. In one embodiment, the surfactant or polymer is selected so that the surfactant or polymer adsorbs on the surface of the lignin to prevent the enzyme adsorption onto the surface of the lignin. In one embodiment, the additive (4) is added such that an amount of the dry matter of the surface active compound is 0.01-2%, in one embodiment 0.05-1.5% and in one embodiment 0.1-1%, by weight of the solid matter, e.g. of the dry matter of the feed to the enzymatic hydrolysis stage (2).

In one embodiment, a make-up enzyme (3), such as new enzyme, make-up enzyme or fresh enzyme, is added in connection with the enzymatic hydrolysis stage (2), such as before or during the enzymatic hydrolysis stage (2), or to the plant based feed (1), to the plant based material (10) and/or to a pre-mixing stage (21). In one embodiment, the make-up enzyme (3) is added to the plant based feed (1) and/or to the enzymatic hydrolysis stage (2). In one embodiment, the make-up enzyme (3) is added in the pre-mixing stage (21) or before the pre-mixing stage (21). In one embodiment, the make-up enzyme (3) is added before the enzymatic hydrolysis stage (2). In one embodiment, the make-up enzyme (3) is added to the plant based feed (1), e.g. in a pipe or tube before the enzymatic hydrolysis stage (2) or before the enzymatic hydrolysis reactor. In one embodiment, the make-up enzyme (3) is added to the enzymatic hydrolysis stage (2). In one embodiment, the make-up enzyme is added to the plant based material (10). In one embodiment, the make-up enzyme (3) is added in connection with the first enzymatic hydrolysis step of the enzymatic hydrolysis stage (2). In one embodiment, the apparatus comprises at least one second enzyme addition device for adding the make-up enzyme (3). Preferably, the make-up enzyme (3) is added to the stage or step or to the flow in which the process conditions are favorable for the enzyme used in the process or in which the enzyme is not denatured. Preferably, the make-up enzyme dose and composition is optimized based on the material of the feed, properties of the enzyme and/or desired conversion. In one embodiment, the enzyme dose of the make-up enzyme (3) which is added is equal or less than the dose of an initial enzyme (23) in the initial feed batch (22). In one embodiment, the enzyme dose of the make-up enzyme (3) which is added is higher than the dose of an initial enzyme (23) in the initial feed batch (22), for example in a desired or in a predetermined recycling cycle or cycles. In one embodiment, the make-up enzyme dose is 5-200%, in one embodiment 10-100%, in one embodiment 20-80%, in one embodiment 30-70%, by weight from the enzyme dose of the initial feed batch. In one embodiment, the make-up enzyme dose is 2-50%, in one embodiment 5-30%, in one embodiment 10-20%, by weight from the enzyme dose of the initial feed batch. In one embodiment, the make-up enzyme dose is 100-200% by weight from the enzyme dose of the initial feed batch. In one embodiment, the composition of the make-up enzyme (3) which is added is different than the composition of the initial enzyme (23) in the initial feed batch (22) and the composition of the enzyme (23,3) which is recirculated. In one embodiment, the composition of the make-up enzyme (3) which is added is similar than the composition of the initial enzyme (23) in the initial feed batch (22). Preferably, the dose and composition of the enzyme is optimized and modified during the process. In one embodiment, the enzymatic hydrolysis stage (2) to which the solid fraction (14) comprising the enzyme is recirculated back is carried out without make-up enzyme addition. In one embodiment, the make-up enzyme is added if it is needed based on process conditions. In one embodiment, the make-up enzyme is added in a desired recycling cycle. Preferably, the enzyme (23,3) is added after the addition of the additive (4) for preventing an enzyme adsorption.

In one embodiment, the method comprises at least one pre-mixing stage (21) in connection with or before the enzymatic hydrolysis stage (2). In the pre-mixing stage (21) the starting material (20) is treated by mixing, and an initial feed batch (22) or plant based material (10) is formed. In one embodiment, the starting material (20) is fed to the pre-mixing stage (21) to form by mixing the initial feed batch (22) to the enzymatic hydrolysis stage (2). In one embodiment, some additive components or agents may be added to the starting material. In one embodiment, the additive (4) for preventing an enzyme adsorption may be added to the starting material in the pre-mixing stage (21). In one embodiment, the starting material is mixed after the addition of the additive (4). In one embodiment, the initial (23) or make-up (3) enzyme may be added to the starting material in the pre-mixing stage (21). Preferably, the enzyme (23,3) is added after the addition of the additive (4) for preventing an enzyme adsorption. In one embodiment, the apparatus comprises at least one pre-mixing device which may be selected from the group consisting of a mixer, screw mixer, pump, other suitable device or their combination.

In one embodiment, the pre-mixing stage (21) comprises a mixing wherein sufficient shear force is provided for mixing liquid and solids into a homogenous mixture during the pre-mixing. Further, solids can be disintegrated by means of the effective mixing. Solid particles can break down leading to higher specific surface. In one embodiment, material temperature may be increased by 5-15° C. during the pre-mixing stage (21).

In one embodiment, the initial feed batch is formed from the starting material (20) and is fed as the plant based feed (1) to an enzymatic hydrolysis stage (2) for starting the enzymatic hydrolysis. In one embodiment, the initial feed batch (22) is fed as the plant based feed (1) from the pre-mixing stage (21) to the enzymatic hydrolysis stage (2). In one embodiment, the initial feed batch (22) is formed in the pre-mixing stage (21). In one embodiment, the initial feed batch (22) is formed in a line, such as in a pipe or tube, before the enzymatic hydrolysis stage (2). In one embodiment, the initial feed batch (22) is formed in the enzymatic hydrolysis stage (2). In one embodiment, the initial enzyme (23) is added to the initial feed batch (22), to the enzymatic hydrolysis stage (2) and/or to the pre-mixing stage (21). In one embodiment, the initial enzyme (23) is added to the initial feed batch (22) before the enzymatic hydrolysis stage (2) or in the enzymatic hydrolysis stage (2). In one embodiment, the initial enzyme (23) is mixed to the initial feed batch (22) in the pre-mixing stage (21). Preferably, the initial enzyme (23) is added to the stage or step or to the flow in which the process conditions are favorable for the enzyme used in the process or in which the enzyme is not denatured. In one embodiment, the apparatus comprises at least one first enzyme addition device for adding an initial enzyme (23) to the initial feed batch (22), to the enzymatic hydrolysis stage (2), and/or to the pre-mixing stage (21). In one embodiment, the enzyme dose of the initial feed batch (22) is equal or higher than the make-up enzyme dose in the plant based feed (1) during the state of equilibrium of the process. In one embodiment, the enzyme dose of the initial feed batch (22) is less than the make-up enzyme dose in the plant based feed (1) in at least one recycling cycle. In one embodiment, the additive (4) for preventing an enzyme adsorption is added to the initial feed batch (22), to the pre-mixing stage (21), to the enzymatic hydrolysis stage (2), before or during the enzymatic hydrolysis stage (2), and/or to the hydrolysed product (5). In one embodiment, the additive (4) for preventing an enzyme adsorption is mixed with the starting material (20) in the pre-mixing stage (21). In one embodiment, the additive (4) for preventing an enzyme adsorption is added to the initial feed batch (22) before the enzymatic hydrolysis stage (2) or in the enzymatic hydrolysis stage (2). Preferably, the initial enzyme (23) is added after the addition of the additive (4) for preventing an enzyme adsorption. In one embodiment, the composition of the additive (4) which is added to the initial feed batch (22) may be similar or different than the composition of the additive (4) which is added to the plant based feed (1) after the starting of the enzymatic hydrolysis.

In one embodiment, the starting material is treated in the pre-mixing stage (21) to form a treated flow (10b) of the starting material which is supplied as the plant based material (10) from the pre-mixing stage (21) to the mixing stage (9). In one embodiment, an untreated flow (10a) of the starting material (20) is used directly as the plant based material (10).

In one embodiment, the pre-mixing stage (21) is an intermediate storage of the starting material (20).

In one embodiment, conditions, e.g. pH, temperature and/or consistency, are adjusted and optimized for suitable level for the enzyme in the pre-mixing stage (21). In one embodiment, conditions, e.g. pH, temperature and/or consistency, are adjusted and optimized for suitable level for the enzyme in a line before the enzymatic hydrolysis stage (2) or during the enzymatic hydrolysis stage (2). In one embodiment, conditions, e.g. pH, temperature and/or consistency, are adjusted and optimized for suitable level for the enzyme in a line of the plant based material (10). In one embodiment, dilution water is added in the pre-mixing stage (21). In one embodiment, dilution water is added to the plant based feed (1).

In one embodiment, temperature of the enzymatic hydrolysis stage (2) is adjusted by means of temperature of the dilution liquid and/or by means of other suitable temperature control. In one embodiment, temperature is adjusted so that it is favorable for the enzyme used in the process.

In one embodiment, pH is adjusted before the enzymatic hydrolysis stage (2), e.g. in the pre-mixing stage (21) or before the pre-mixing stage, or in a line before the enzymatic hydrolysis stage (2), or during the enzymatic hydrolysis stage. In one embodiment, pH is between 3-8, in one embodiment between 3.5-7 and in one embodiment between 4-6. In one embodiment, pH is adjusted so that pH is favorable for the enzyme used in the process.

In one embodiment, dewatering is carried out after the enzymatic hydrolysis stage (2).

In one embodiment, the hydrolysed product (5) is cooled after the enzymatic hydrolysis stage (2) so that temperature of the hydrolysed product is 20-30° C. before the first solid-liquid separation stage (6).

In one embodiment, the hydrolysed product (5) is cooled by at least 10° C. In one embodiment, the hydrolysed product (5) is cooled by means of a heat exchanger.

Preferably, the method and apparatus comprises at least one first solid-liquid separation stage (6) preferably after the enzymatic hydrolysis stage (2). In one embodiment, the apparatus comprises at least one first solid-liquid separation device. In one embodiment, the method and apparatus comprise more than one first solid-liquid separation stages. In one embodiment, the apparatus comprises more than one first solid-liquid separation devices. In one embodiment, the first solid-liquid separation stage comprises at least one solid-liquid separation device. In one embodiment, the first solid-liquid separation stage comprises more than one solid-liquid separation devices. In one embodiment, the first solid-liquid separation stage comprises one solid-liquid separation device. In one embodiment, the solid-liquid separation devices are arranged in parallel. In one embodiment, the solid-liquid separation devices are arranged sequentially. In one embodiment, the liquid composition (8) is separated from the lignin fraction (7) by means of at least one solid-liquid separation device. In one embodiment, one solid-liquid separation device can be used in one or more first solid-liquid separation stages (6). In one embodiment, the separation device comprises one or more separation step, e.g. separation segment. The first solid-liquid separation stage may comprise one or more separation steps. In one embodiment, the solid-liquid separation stage comprises different procedures which may be done in one or more separation steps. In one embodiment, the liquid composition (8) is separated in one step. Alternatively, the liquid composition (8) may be separated in more than one steps. In one embodiment, the liquid material is separated in each separation step in order to form the liquid composition (8).

In one embodiment, at least one first solid-liquid separation stage (6) is arranged in connection with the enzymatic hydrolysis stage (2). In one embodiment, at least one first solid-liquid separation stage (6) is arranged after the enzymatic hydrolysis stage (2). In one embodiment, one first solid-liquid separation stage (6) is arranged after the last enzymatic hydrolysis step or reactor of the enzymatic hydrolysis stage (2). In one embodiment, the first solid-liquid separation stage (6) is arranged after all the enzymatic hydrolysis stages (2). In one embodiment, the first solid-liquid separation stage (6) is arranged after each enzymatic hydrolysis stage (2).

In one embodiment, the method and apparatus comprise more than one enzymatic hydrolysis stages (2) or enzymatic hydrolysis devices which are arranged in parallel and one first solid-liquid separation stage (6) after the enzymatic hydrolysis stages (2) or enzymatic hydrolysis devices. In one embodiment, the method and apparatus comprises one or more combination of enzymatic hydrolysis stage (2) and first solid-liquid separation stage (6). Said combinations may be arranged sequentially and/or in parallel.

Preferably, the method and apparatus comprises at least one second solid-liquid separation stage (13) preferably after the mixing stage (9). In one embodiment, the apparatus comprises at least one second solid-liquid separation device. In one embodiment, the method and apparatus comprises more than one second solid-liquid separation stages. In one embodiment, the apparatus comprises more than one second solid-liquid separation devices. In one embodiment, the second solid-liquid separation stage comprises at least one solid-liquid separation device. In one embodiment, the second solid-liquid separation stage comprises more than one solid-liquid separation devices. In one embodiment, the second solid-liquid separation stage comprises one solid-liquid separation device. In one embodiment, the liquid fraction (15) is separated from the solid fraction (14) by means of one solid-liquid separation device. In one embodiment, one solid-liquid separation device can be used in one or more second solid-liquid separation stages (13). In one embodiment, the separation device comprises one or more separation step, e.g. separation segment. The second solid-liquid separation stage may comprise one or more separation steps. In one embodiment, the solid-liquid separation stage comprises different procedures which may be done in one or more separation steps. In one embodiment, the liquid fraction (15) is separated in one step. Alternatively, the liquid fraction (15) may be separated in more than one steps. In one embodiment, the liquid material is separated in each separation step in order to form the liquid fraction (15).

In one embodiment, at least one second solid-liquid separation stage (13) is arranged in connection with the mixing stage (9). In one embodiment, one second solid-liquid separation stage (13) is arranged after the mixing stage (9). In one embodiment, one second solid-liquid separation stage (13) is arranged after the last mixing step or reactor of the mixing stage (9).

Preferably, the first and second solid-liquid separation stages (6,13) comprise the separation of the liquid material, such as the liquid composition (8) and liquid fraction (15), from the solid material, such as the lignin fraction (7) and solid fraction (14). In one embodiment, the liquid material is separated from the solid material by means of filtration, centrifugal treatment or their combinations. In one embodiment, the filtration is carried out by pressure, underpressure or overpressure.

The first and/or second solid-liquid separation stage comprises at least one solid-liquid separation device. In one embodiment, the first and second solid-liquid separation device is based on a counter-current washing. In one embodiment, the solid-liquid separation device is selected from the group consisting of filtration device, vacuum filtration device, press filter, belt press, centrifugal device, screw press and their combinations. In one embodiment, the solid-liquid separation device is selected from the group consisting of pressure filtration device, vacuum filtration device, filtration device based on underpressure, filtration device based on overpressure, filter press, other suitable press, centrifugal device and their combinations. In one embodiment, the solid-liquid separation device is a pressure filtration device, vacuum filtration device, filtration device based on underpressure or filtration device based on overpressure. In one embodiment, the solid-liquid separation device is a belt press, twin wire press or centrifuge. Alternatively, the solid-liquid separation device can be another washing device in which low amount of washing water is used and washing is done in high dry matter content. Then good recovery can be achieved. Alternatively, the solid-liquid separation device may be any suitable separation device.

In one embodiment, the solid-liquid separation stage (6,13) comprises a filtration in which the liquid composition (8) or liquid fraction (15) is separated in a liquid form from solid material, such lignin fraction (7) or solid fraction (14). Preferably, pressure is used in the filtration. In one embodiment, liquid is separated by a pressure difference, such as by means of vacuum or overpressure. In one embodiment, the solid-liquid separation stage comprises a washing in which a displacement washing is carried out with small amount clean water in order to remove majority of sugars, inhibitors and other soluble compounds from the solid material (7,14) and to provide high recovery of soluble compounds. Preferably, ratio of washing water to solid is below 6, preferably below 3 and more preferably below 1.5. In one embodiment, the solid-liquid separation stage (6,13) comprises the filtration and washing. Preferably, high concentration and recovery of soluble material in the liquid phase can be achieved with small amount of clean water. Further, the solid material with minor amount of soluble compounds, or the solid material which is substantially free of soluble compounds, or the soluble compound lean solid material, can be achieved.

In one embodiment, the solid-liquid separation (6,13) is made by means of a pressure filtration. In one embodiment, the apparatus comprises at least one pressure filtration device as the solid-liquid separation device.

In the different solid-liquid separation stages the separation can be carried out by means of similar or different separation methods or separation devices.

The liquid composition (8) and plant based material (10) are supplied to the mixing stage (9) for forming the mixture (11). Preferably, the sufficient amount of the plant based material (10) is mixed to the liquid composition (8) to form the mixture (11) in the mixing stage (9) such that the whole liquid composition (8) is in contact with the solid material of the plant based material (10) in order to recover the enzyme. The liquid composition and plant based material are treated in one or more than one mixing stages (9) for forming the mixture (11). In one embodiment, the mixing stage comprises one or more than one mixing steps. The mixing stage (9) may comprise a vessel, reactor, mixer, e.g. in-line mixer or static mixer, pump, line, tube, pipe or other suitable means in which the mixing can be carried out. In one embodiment, the mixing is carried out in a vessel, reactor, mixer, pump, line, tube or pipe of the mixing stage (9). In one embodiment, the mixing stage (9) is a re-adsorption stage. In one embodiment, the mixing stage (9) is a conditioning stage. In one embodiment, the re-adsorption is performed in the mixing stage (9). During the re-adsorption, at least a part of the enzyme (23,3), in one embodiment the most of the enzyme (23,3), is attached and adsorbed on the solid material surface of the mixture (11), preferably on non-lignin surface. In one embodiment, desired additive agent or agents (12) may be added to the mixture (11) in connection with the mixing stage (9). In one embodiment, the additive (4) for preventing an enzyme adsorption is added to the plant based material (10) before the mixing stage (9), in the mixing stage (9) and/or in the pre-mixing stage (21). In one embodiment, the additive (4) for preventing an enzyme adsorption is selected so that said additive or its active part has adhesion ability to the lignin surface.

In one embodiment, a residence time of the mixing stage (9) is below 30 min, in one embodiment below 20 min, in one embodiment below 15 min, in one embodiment below 10 min, in one embodiment below 5 min or in one embodiment below 1 min. In one embodiment, a residence time of the mixing stage (9) is below 120 min, in one embodiment below 90 min or in one embodiment below 60 min.

In one embodiment, conditions, e.g. consistency, pH and/or temperature, are adjusted and optimized for suitable level for the enzyme in connection with the mixing stage (9). In one embodiment, the dry matter of the mixture (11) is 2-60%, in one embodiment 4-40% and in one embodiment 5-20%, by weight (TS, total solids, at 105° C.) after mixing stage (9).

The mixture (11) formed in the mixing stage (9) is supplied to the second solid-liquid separation stage (13). At least a part of the solid fraction (14) or the whole solid fraction (14) which comprises the enzyme (23,3) is recirculated from the second solid-liquid separation stage (13) to the enzymatic hydrolysis stage (2). In one embodiment, a part of the solid fraction (14) is recovered, and is not recirculated to the enzymatic hydrolysis stage (2). In one embodiment, a part of the mixture (11) may be supplied past the second solid-liquid separation stage (13). It has been observed that the enzyme is going on the solid fraction (14) and the enzyme can be supplied back to the enzymatic hydrolysis stage (2) together with the solid fraction (14). In one embodiment, the enzyme is selected so that the enzyme has adhesion ability to the solids. In one embodiment, the recycled enzyme is activated during the mixing.

In one embodiment, conditions, e.g. pH, temperature and/or consistency, are adjusted and optimized for suitable level for the enzyme in a line between the second solid-liquid separation stage (13) and the enzymatic hydrolysis stage (2). In one embodiment, the solid fraction (14) is diluted before the enzymatic hydrolysis stage (2).

In one embodiment, the additive (4) for preventing an enzyme adsorption is added to the solid fraction (14) and/or to the plant based feed (14,1) and/or to the enzymatic hydrolysis stage (2). In one embodiment, the make-up enzyme (3) is added to the solid fraction (14) and/or to the plant based feed (14,1) and/or to the enzymatic hydrolysis stage (2). Preferably the make-up enzyme (3) is added after the addition of the additive (4). Preferably, the make-up enzyme (3) is added to the stage or step or to the flow in which the process conditions are favorable for the enzyme used in the process or in which the enzyme is not denatured.

In one embodiment, the solid fraction (14) which comprises the enzyme (23,3) is fed as the plant based feed (1) to the enzymatic hydrolysis stage (2), and the make-up enzyme (3) is added to the plant based feed (1) or to the enzymatic hydrolysis stage (2).

In one embodiment, the method comprises below 30, in one embodiment below 25, in one embodiment below 20 and in one embodiment below 15, recycling cycles of the solid fraction (14). In one embodiment, the method comprises over 2, in one embodiment over 3, in one embodiment over 5 and in one embodiment over 7, recycling cycles of the solid fraction (14). In one embodiment, the method comprises 2-30, in one embodiment 3-25, in one embodiment 5-20 and in one embodiment 7-15, recycling cycles of the solid fraction (14). In one embodiment, the liquid fraction (15) is the liquid composition (8) in the last recycling cycle.

In one embodiment, the solid fraction (14) is fed to the desired step of the enzymatic hydrolysis stage (2).

In one embodiment, the plant based material (10) is added, preferably as an additional feed, to the plant based feed (1) or to the enzymatic hydrolysis stage (2). In one embodiment, the starting material (20) is added, preferably as an additional feed, to the plant based feed (1) or to the enzymatic hydrolysis stage (2). In one embodiment, the apparatus comprises at least one means for supplying the plant based material (10) to the mixing stage (9). In one embodiment, the apparatus comprises at least one means for supplying the plant based material (10) and/or starting material (20) to the plant based feed (1) or to the enzymatic hydrolysis stage (2). In one embodiment, the means for supplying the plant based material is selected from the group consisting of pump, pipe, tube, duct, conduit, channel, outlet, other suitable feeding device and their combinations.

In one embodiment, the apparatus comprises at least one means for supplying the intermediate product, such as hydrolysed product (5) from the enzymatic hydrolysis stage (2) to the first solid-liquid separation stage (6). In one embodiment, the apparatus comprises at least one means for supplying the intermediate product, such as mixture (11) from the mixing stage (9) to the second solid-liquid separation stage (13). In one embodiment, the means for supplying the intermediate product (5,11) is selected from the group consisting of conveyor, e.g. chain conveyor, belt conveyor, flight conveyor or other conveyor, screw, belt, pump, pipe, tube, duct, conduit, channel, outlet, other suitable feeding device and their combinations.

In one embodiment, the apparatus comprises at least one means for supplying the liquid composition (8) to the mixing stage (9). The means for supplying the liquid composition is selected from the group consisting of pump, pipe, tube, duct, conduit, channel, outlet, other suitable feeding device and their combinations.

In one embodiment, the apparatus comprises at least one means or at least one device for recirculating or supplying at least a part of the solid fraction (14) comprising enzyme, as the plant based feed (1), to the enzymatic hydrolysis stage (2).

In one embodiment, the apparatus comprises at least one means for recovering the lignin fraction (7) or its part after the first solid-liquid separation stage (6). In one embodiment, the means for recovering the lignin fraction is selected from the group consisting of assembly, outlet, conveyor, e.g. chain conveyor, belt conveyor, flight conveyor or other conveyor, screw, belt, pipe, tube, duct, discharge outlet, discharge valve, discharge channel, conduit, other suitable device and their combinations.

In one embodiment, at least one liquid fraction (15) is recovered after the second solid-liquid separation stage (13). In one embodiment, the apparatus comprises at least one means for recovering at least one liquid fraction after the second solid-liquid separation stage (13). In one embodiment, the means for recovering the liquid fraction is selected from the group consisting of assembly, outlet, pipe, tube, duct, discharge outlet, discharge valve, discharge channel, conduit, other suitable device and their combinations.

In one embodiment, the liquid fraction (15) is formed by means of the method. In one embodiment, the liquid fraction comprises soluble C5 and C6 carbohydrates after the enzymatic hydrolysis stage (2). In one embodiment, the liquid fraction comprises at least soluble C6 carbohydrates. In one embodiment, the liquid fraction comprises soluble C6 carbohydrates, preferably over 50% by weight, and further it may comprise also C5 carbohydrates, preferably below 50%, more preferably below 30%, more preferably below 20% and the most preferably below 10%, by weight of the carbohydrates. Preferably, the liquid fraction (15) can contain other monosaccharides, disaccharides, oligosaccharides and/or polysaccharides. In one embodiment, the liquid fraction (15) contains galactose, glucose, mannose, arabinose, xylose, glucuronic acid and galacturonic acid. Preferably, the liquid fraction (15) is in the form of solution.

In one embodiment, at least a part of the liquid fraction (15) is recovered by supplying out from the second solid-liquid separation stage (13).

In one embodiment, the liquid fraction (15) comprises C6 carbohydrates over 80% by weight, preferably over 90% by weight, the most preferably over 95% by weight, of the carbohydrates. Preferably, the liquid fraction (15) is a glucose rich fraction. Then the liquid fraction (15) is sufficient pure that it can be used as such, or it can be concentrated and utilized after the concentration.

The liquid fraction (15) may be used as component in manufacturing a final product. The liquid fraction from the solid-liquid separation stages (13) can be utilized separately, or it can be combined or mixed with a suitable fraction or component and utilized as a mixture. In one embodiment, the liquid fraction is used as such. In one embodiment, the liquid fraction is supplied to a further processing. In one embodiment, the liquid fraction is purified. In one embodiment, the liquid fraction is concentrated. In one embodiment, the monomerization of the liquid fraction is made before the further processing. In one embodiment, the liquid fraction is supplied to a fermentation process. In one embodiment, the liquid fraction is used as a source material in the fermentation. In one embodiment, the liquid fraction is supplied to a hydrolysis process. In one embodiment, the liquid fraction is used as a source material in the hydrolysis, such as in the acid hydrolysis, enzymatic hydrolysis or the like. In one embodiment, the liquid fraction is supplied to a chemical treatment process. In one embodiment, the liquid fraction is used as a source material in the chemical treatment. In one embodiment, the liquid fraction is supplied to a polymerization process. In one embodiment, the liquid fraction is used as a source material in the polymerization process. In one embodiment, the liquid fraction is supplied to a depolymerization process. In one embodiment, the liquid fraction is used as a source material in the depolymerization process. In one embodiment, the liquid fraction is supplied to a catalytic treatment process. In one embodiment, the liquid fraction is used as a source material in the catalytic treatment.

In one embodiment, the liquid fraction is supplied to a degradation process. In one embodiment, the liquid fraction is used as a source material in the degradation process. In one embodiment, the liquid fraction is supplied to an enzymatic treatment. In one embodiment, the liquid fraction is used as a source material in the enzymatic treatment. In one embodiment, the liquid fraction is supplied to a manufacture of binder. In one embodiment, the liquid fraction is used as a source material in the manufacture of binder. In one embodiment, the liquid fraction is supplied to a manufacture of feed. In one embodiment, the liquid fraction is used as a source material in the manufacture of feed. In one embodiment, the liquid fraction is supplied to a manufacture of food. In one embodiment, the liquid fraction is used as a source material in the manufacture of food. The liquid fraction may be supplied directly to the fermentation, hydrolysis, chemical treatment, catalytic treatment, polymerization process, depolymerization process, degradation process, enzymatic treatment, manufacture of binder, manufacture of feed, manufacture of food or other suitable process or their combinations, or alternatively via a suitable treatment step or an additional step, e.g. additional concentration step or purification step, to the fermentation, hydrolysis, chemical treatment, catalytic treatment, polymerization process, depolymerization process, degradation process, enzymatic treatment, manufacture of binder, manufacture of feed, manufacture of food or other suitable process or their combinations.

Preferably, the lignin fraction (7) comprising solids is formed by means of the method. Preferably, the lignin fraction (7) comprises lignin after the first solid-liquid separation stage (6). In one embodiment, the lignin fraction comprises lignin and solid carbohydrates, such as C6 carbohydrates, such as ($C_6H_{12}O_6$ or $(C_6(H_2O)_n)$), and other solid carbohydrates after the solid-liquid separation stage. Further, the lignin fraction may comprise some residual soluble material. In one embodiment, the lignin fraction is in the solid form. In one embodiment, dry matter content of the lignin fraction is over 20% by weight, preferably over 30% by weight, more preferably over 40% by weight, most preferably over 50% by weight, after the first solid-liquid separation stage. In one embodiment, the lignin fraction contains soluble compounds below 15%, preferably below 6%, more preferably below 3% by weight, after the first solid-liquid separation stage. In one embodiment, an amount of carbohydrates is below 25% by weight, preferably below 10% by weight, more preferably below 5% by weight, in the lignin fraction.

In one embodiment, at least a part of the lignin fraction (7) is recovered after the first solid-liquid separation stage (6). In one embodiment, the lignin fraction (7) is supplied out after the solid-liquid separation stage (6). In one embodiment, a part of the lignin fraction (7) may be recirculated to the enzymatic hydrolysis stage (2).

The lignin fraction (7) may be used as component in manufacturing a final product. In one embodiment, the lignin fraction is used as such. In one embodiment, the lignin fraction is supplied to a further processing. In one embodiment, the lignin fraction (7) is supplied to a lignin purification for forming purified lignin. In one embodiment, the lignin fraction is supplied to a lignin separation for separating lignin from the lignin fraction. In one embodiment, the lignin fraction is supplied to a hydrolysis which may be selected from the group consisting of acid hydrolysis, enzymatic hydrolysis, supercritical hydrolysis and/or subcritical hydrolysis and their combinations, or to a polymerization process, a depolymerization process, a degradation process, a chemical treatment, a manufacture of a composite material, lignin composite, activated carbon, carbon fiber, binder material, polymers, resins, phenolic component, dispersion agent or absorbent material, a manufacture of feed or food, or a combustion process or other suitable process or their combinations. The lignin fraction may be supplied directly to the hydrolysis, polymerization process, depolymerization process, degradation process, chemical treatment, manufacturing processes of said materials, combustion process or other suitable process, or alternatively via a suitable treatment step or an additional step, e.g. additional separation step, purification step or dewatering step, to the hydrolysis, polymerization process, depolymerization process, degradation process, chemical treatment, manufacturing processes of said materials, combustion process or other suitable process.

By means of the method and the apparatus the enzymatic hydrolysis can be improved and the enzyme dosage can be decreased. The enzymes can be recycled in the method or in the apparatus. Then the costs of the enzymes may be decreased in the process. Further, by means of the method and the apparatus residence time or reaction time of the enzymatic hydrolysis can be shortened, consistency can be increased in the enzymatic hydrolysis, purity of lignin can be improved, and/or the conversion of carbohydrates can be improved. In the method and apparatus an effective enzymatic hydrolysis can be achieved.

The method and the apparatus provide the lignin fraction and liquid fraction with good quality. The lignin fraction has very high concentration of lignin. Further, the lignin fraction has very high purity. Also the recovery of the liquid fraction and lignin fraction can be improved. Also the carbohydrate recovery and conversion can be improved. Further, the method and the apparatus decrease post-treating costs of the lignin fraction and also liquid fraction. Further, raw material with inhibitors and undesired agents can be used as a source material in the process. Further, the method and the apparatus can be used for treating materials comprising inhibitors, coming from cellulose based material. According to an example, the inhibitor may belong to the group consisting of soluble lignin, organic acids, dissolved salts, glucose, xylose, oligomers, or other inhibitors or their combinations.

The method and the apparatus provide an industrially applicable, simple and affordable way of carrying out the enzymatic hydrolysis. The method or the apparatus is easy and simple to realize as a production process. The method and the apparatus are suitable for use in the manufacture of the different lignin and carbohydrate fractions and final products from different starting materials.

EXAMPLES

Some embodiments of the invention are described in more detail by the following examples with reference to accompanying drawings.

Example 1

In this example, the enzymatic hydrolysis comprising a predetermined enzyme dose is carried out in which the enzyme is recirculated, and a lignin fraction and liquid fraction are produced according to a process of FIG. 1.

Firstly, an initial feed batch (22) is formed from starting material (20) and is fed as a plant based feed (1) into an enzymatic hydrolysis stage (2). The starting material (20) has been treated by means of pre-treatment, e.g. by physical, chemical or physic-chemical treatment such as by microwave or ultra-sound treatment, or by steam explosion. The starting material (20) is supplied to a pre-mixing stage (21) in which it is mixed for forming the initial feed batch (22). The initial feed batch (22) is fed as the plant based feed (1) by means of a feeding device into the batch enzymatic hydrolysis stage (2). An additive (4) for preventing an enzyme adsorption which comprises at least one surfactant is added to the initial plant based feed (22,1) in a line to the enzymatic hydrolysis stage (2). Also an initial enzyme (23) is added to the initial plant based feed (22,1), in this example after the addition of the additive (4), in the line to the enzymatic hydrolysis stage (2). Alternatively, the initial enzyme (23) may be added in the enzymatic hydrolysis stage (2). Preferably, the surfactant is amphiphilic compound, hydrophilic compound, non-ionic compound and/or anionic compound, e.g. polysorbate, polyoxyethylene or polyethylene glycol.

The plant based feed (1) may be diluted with liquid, such as water, before the enzymatic hydrolysis stage (2). After the enzymatic hydrolysis stage (2), the apparatus comprises a first solid-liquid separation stage (6) comprising a filtration device or a centrifugal device. A hydrolysed product (5) from the enzymatic hydrolysis stage (2) is supplied to the first solid-liquid separation stage (6). A liquid composition (8) comprising soluble C5 and C6 carbohydrates and the enzyme is separated from a lignin fraction (7) in the first solid-liquid separation stage (6). The liquid composition (8) is supplied to a mixing stage (9).

The lignin fraction (7) comprising lignin, solid carbohydrates, some soluble sugar, monomer, oligomer and polymer residual and also a main part of the surfactant is removed from the first solid-liquid separation stage (6) and recovered.

The liquid composition (8) comprising the enzyme, and a plant based material (10) are supplied to the mixing stage (9) in which said components are mixed, a re-adsorption is made and a mixture (11) is formed. The plant based material (10) is a treated flow (10b) of the starting material (20) which is treated in the pre-mixing stage (21). Alternatively, the plant based material (10) is an untreated flow (10a) of the starting material (20). Desired additive agents (12) may be added to the mixture (11) in the mixing stage (9). The mixture (11) is supplied to the second solid-liquid separation stage (13) in which a liquid fraction (15) and solid fraction (14) are separated.

At least a part of the solid fraction (14) comprising the enzyme is recirculated by means of a recirculation device as the plant based feed (1) back to the enzymatic hydrolysis stage (2). The additive (4) comprising at least one surfactant is added to the enzymatic hydrolysis stage (2), or alternatively to the recirculated plant based feed (14,1). A make-up enzyme (3) is added to the enzymatic hydrolysis stage (2), or alternatively to the recirculated plant based feed (14,1), in this example after the addition of the additive (4). Alternatively, the make-up enzyme (3) is not added, or the make-up enzyme is added if it is needed or in the predetermined recycling cycle. Also, the plant based material (10), i.e. treated (10b) or untreated (10a) starting material (20), or alternatively the starting material (20), may be added as an additional feed to the plant based feed (1) or to the enzymatic hydrolysis stage (2). The plant based feed (1) may be diluted with liquid, such as water, before the enzymatic hydrolysis stage (2).

The liquid fraction (15) is recovered from the second solid-liquid separation stage (13). The apparatus may comprise means for supplying the liquid fraction (15) out from the apparatus or means for supplying the liquid fraction (15) to the next treatment stage.

Example 2

In this example, the enzymatic hydrolysis is carried out according to a process of Example 1 and FIG. 1.

An additive (4) for preventing an enzyme adsorption which comprises at least one surfactant is added to the starting material (20) in the pre-mixing stage (21) to form the initial plant based feed (22,1). The additive (4) is not added to the initial plant based feed (22,1) in a line to the enzymatic hydrolysis stage (2) such as in Example 1. An initial enzyme (23) is added to the initial plant based feed (22,1) after the addition of the additive (4), e.g. in the line to the enzymatic hydrolysis stage (2). Alternatively, the initial enzyme (23) may be added in the enzymatic hydrolysis stage (2) or in the pre-mixing stage (21).

Example 3

In this example, the enzymatic hydrolysis is carried out according to a process of Example 1 and FIG. 1.

An additive (4) for preventing an enzyme adsorption which comprises at least one surfactant may be added to the treated flow (10b) of the starting material (20) in the pre-mixing stage (21) or to the plant based material (10) before the mixing stage (9) or in the mixing stage (9). The additive (4) is not added to the enzymatic hydrolysis stage (2), or to the recirculated plant based feed (14,1). A make-up enzyme (3) is added to the enzymatic hydrolysis stage (2), or to the recirculated plant based feed (14,1).

Example 4

In this example, the enzymatic hydrolysis is carried out according to a process of Example 1 and FIG. 1.

An additive (4) for preventing an enzyme adsorption which comprises at least one surfactant is added to the recirculated plant based feed (14,1), and a make-up enzyme (3) is added to the enzymatic hydrolysis stage (2). Alternatively, the make-up enzyme (3) is added to the recirculated plant based feed (14,1) after the addition of the additive (4).

Example 5

In this example, the enzymatic hydrolysis comprising a predetermined enzyme dose is carried out in which the enzyme is recirculated, and a lignin fraction and liquid fraction are produced according to a process of FIG. 2.

Firstly, an initial feed batch (22) is formed from starting material (20) and is fed as a plant based feed (1) into an enzymatic hydrolysis stage (2). The starting material (20) has been treated by means of pre-treatment, e.g. by physical, chemical or physic-chemical treatment such as by microwave or ultra-sound treatment, or by steam explosion. An additive (4) for preventing an enzyme adsorption which comprises at least one surfactant is added to the starting material (20) to form the initial plant based feed (22,1) in a line before the enzymatic hydrolysis stage (2). Preferably, the surfactant is amphiphilic compound, hydrophilic compound, non-ionic compound and/or anionic compound. Also an initial enzyme (23) is added to the initial plant based feed (22,1), in this example after the addition of the additive (4), in the line before the enzymatic hydrolysis stage (2). Alternatively, the initial enzyme (23) may be added in the enzymatic hydrolysis stage (2). The initial feed batch (22) is fed as the plant based feed (1) by means of a feeding device into the batch enzymatic hydrolysis stage (2).

The plant based feed (1) may be diluted with liquid, such as water, before the enzymatic hydrolysis stage (2). After the enzymatic hydrolysis stage (2), the apparatus comprises a first solid-liquid separation stage (6) comprising a filtration device or a centrifugal device. A hydrolysed product (5) from the enzymatic hydrolysis stage (2) is supplied to the first solid-liquid separation stage (6). A liquid composition (8) comprising soluble C5 and C6 carbohydrates and the enzyme is separated from a lignin fraction (7) in the first solid-liquid separation stage (6). The liquid composition (8) is supplied to a mixing stage (9).

The lignin fraction (7) comprising lignin, solid carbohydrates, some soluble sugar, monomer, oligomer and polymer residual and also a main part of the surfactant is removed from the first solid-liquid separation stage (6) and recovered.

The liquid composition (8) comprising the enzyme and a plant based material (10) are supplied to the mixing stage (9) in which said components are mixed, a re-adsorption is made and a mixture (11) is formed. The plant based material (10) is an untreated flow (10a) of the starting material (20). The mixture (11) is supplied to the second solid-liquid separation stage (13) in which a liquid fraction (15) and solid fraction (14) are separated.

At least a part of the solid fraction (14) comprising the enzyme is recirculated by means of a recirculation device as the plant based feed (1) back to the enzymatic hydrolysis stage (2). The additive (4) for preventing an enzyme adsorption which comprises at least one surfactant is added to the enzymatic hydrolysis stage (2), or alternatively to the recirculated plant based feed (14,1). A make-up enzyme (3) is added to the enzymatic hydrolysis stage (2), or alternatively to the recirculated plant based feed (14,1) after the addition of the additive (4). Alternatively, the make-up enzyme (3) is not added, or the make-up enzyme is added if it is needed or in the predetermined recycling cycle. Also, the plant based material (10), i.e. the flow (10a) of the starting material (20), may be added as an additional feed to the plant based feed (1) or to the enzymatic hydrolysis stage (2). The plant based feed (1) may be diluted with liquid, such as water, before the enzymatic hydrolysis stage (2).

The liquid fraction (15) is recovered from the second solid-liquid separation stage (13). The apparatus may comprise means for supplying the liquid fraction (15) out from the apparatus or means for supplying the liquid fraction (15) to the next treatment stage.

Example 6

In this example, an enzymatic hydrolysis and a recirculation in connection with an enzymatic hydrolysis process were studied.

The enzymatic hydrolysis process with an enzyme recycling was simulated and compared to a traditional batch hydrolysis process in laboratory scale tests. A dilute acid pretreated, steam exploded and washed hardwood was used as a substrate in the test. Composition of the substrate was: Glucose 57% by weight, Xylose 9% by weight and lignin 31% by weight.

A reference hydrolysis was done in a single step batch process. The hydrolysis with recycling according to FIG. 2 comprises a surfactant. Commercially available enzyme mixture A was used in the hydrolysis. The substrate was diluted by using distilled water, and pH was adjusted to 4.5. Temperature was 45° C. in the enzymatic hydrolysis and retention time was 48 hours in each batch. An enzyme dosage in reference was 5% (based on dry matter content of substrate, total solids TS, at 105° C.). In the case of recycling the first enzyme dosage was 6.5% and following dosages 2.5% (based on dry matter content of substrate, total solids TS, at 105° C.) in the recycled batches. Tests were done in 3 litre reactor at 15% dry matter content (total solids TS, at 105° C.) with stirring. A solid-liquid separation was done using Büchner funnel and glucose content of the liquid phase was analyzed using HPLC standard methods according to SCAN CM 71:09.

Figure 3:
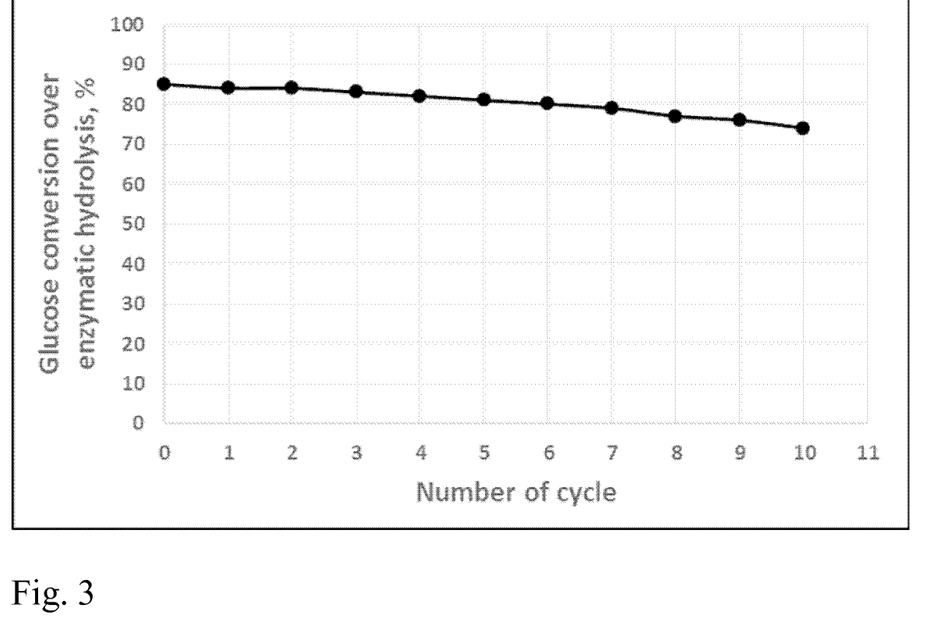
FIG. 3 shows results from one example carried out according to one method embodiment.

Glucose conversion of the reference with 5% dosage was 80.7%. Average enzyme dosage with the recycling after 10 recycling cycles was 2.9% and glucose conversion 80.5%. Conversion level after each cycle is presented in FIG. 3. Savings in enzymes costs with recycling were 40% comparing to the reference in the same glucose conversion level.

Example 7

In this example, an enzymatic hydrolysis and a recirculation in connection with an enzymatic hydrolysis process were studied.

The enzymatic hydrolysis process with an enzyme recycling was simulated and compared to a traditional batch hydrolysis process in laboratory scale tests. A dilute acid pretreated, steam exploded, delignified and washed hardwood was used as a substrate in the test. Composition of the substrate was: Glucose 74% by weight, Xylose 3% by weight and lignin 11% by weight.

A reference hydrolysis was done in a single step batch process. The hydrolysis with recycling according to FIG. 2 comprises a surfactant. Commercially available enzyme mixture B was used in the hydrolysis. The substrate was diluted by using distilled water, and pH was adjusted to 5. Temperature was 50° C. in the enzymatic hydrolysis, and retention time was 48 hours in each batch. An enzyme dosage in reference was 4.5% (based on dry matter content of substrate, total solids TS, at 105° C.). In the case of recycling the first enzyme dosage was 6% and following dosages 1.4% (based on dry matter content of substrate, total solids TS, at 105° C.) in the recycled batches. Tests were done in 3 litre reactor at 15% dry matter content (total solids TS, at 105° C.) with stirring. A solid-liquid separation was done using Buchner funnel and glucose content of the liquid phase was analyzed using HPLC standard methods according to SCAN CM 71:09.

Figure 4:
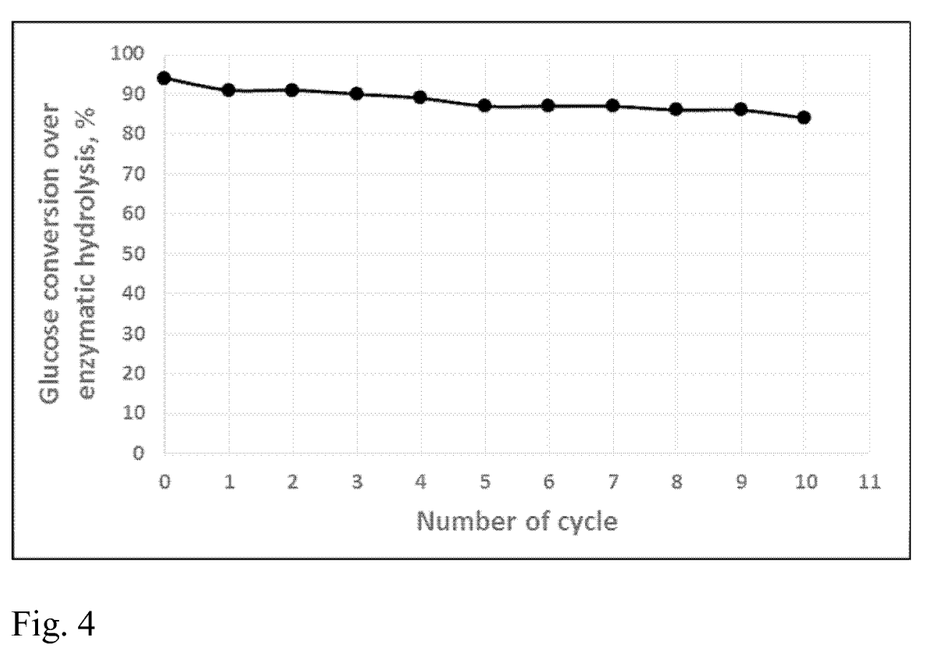
FIG. 4 shows results from one example carried out according to one method embodiment.

Glucose conversion of the reference with 4.5% dosage was 88.9%. Average enzyme dosage with the recycling after 10 recycling cycles was 1.8% and glucose conversion 88.4%. Conversion level after each cycle is presented in FIG. 4. Savings in enzymes costs with recycling were 60% comparing to the reference in the same glucose conversion level.

The method and apparatus according to the present invention is suitable in different embodiments to be used in different enzymatic hydrolysis. Further, the method and apparatus according to the present invention is suitable in different embodiments to be used for producing the most different kinds of liquid and lignin fractions from different raw materials.

The invention is not limited merely to the example referred to above; instead many variations are possible within the scope of the inventive idea defined by the claims.

The invention claimed is:

1. A method for an enzymatic hydrolysis in which a plant based feed is fed to an enzymatic hydrolysis stage in which the plant based feed is hydrolysed by means of an enzyme to form a hydrolysed product, the method comprising:

Treating a starting material by an acid hydrolysis and steam explosion and forming a plant based material, the plant based feed comprising the plant based material;

Feeding an additive for preventing enzyme adsorption (i) to the enzymatic hydrolysis stage, (ii) to the plant based feed, which is fed to the enzymatic hydrolysis stage, (iii) to the plant based material, or (iv) to any combination thereof Adding the enzyme to the enzymatic hydrolysis stage after addition of the additive;

Carrying out the enzymatic hydrolysis to generate the hydrolysed product;

Supplying the hydrolysed product from the enzymatic hydrolysis stage to a first solid-liquid separation stage in which a lignin fraction comprising the additive and a liquid composition which comprises the enzyme are separated;

Mixing the liquid composition with fresh plant based material in a mixing stage after the first solid-liquid separation stage to form a mixture;

Feeding the additive to the fresh plant based material before the mixing stage or during the mixing stage;

Separating a solid fraction which comprises the enzyme, and a liquid fraction from the mixture in a second solid-liquid separation stage after the mixing stage; and Feeding at least a part of the solid fraction which comprises the enzyme to the enzymatic hydrolysis stage.

2. The method according to claim 1, further comprising:
forming an initial feed batch from the plant based material; and
feeding the initial feed batch as the plant based feed to the enzymatic hydrolysis stage.

3. The method according to claim 2, wherein the additive for preventing an enzyme adsorption is added to the plant based material, to a pre-mixing stage, or to any combination thereof.

4. The method according to claim 2, wherein the enzyme is an initial enzyme, and the initial enzyme is added to the initial feed batch, to the enzymatic hydrolysis stage, to a pre-mixing stage, or to any combination thereof.

5. The method according to claim 1, wherein a make-up enzyme is added to the plant based feed, to the enzymatic hydrolysis stage, to the plant based material, to a pre-mixing stage, or to any combination thereof.

6. The method according to claim 1, wherein the plant based feed is a treated flow from a pre-mixing stage.

7. The method according to claim 1, wherein the solid fraction, which comprises the enzyme, is fed to the enzymatic hydrolysis stage, and a make-up enzyme is added to the solid fraction or to the enzymatic hydrolysis stage.

8. The method according to claim 1, wherein the additive comprises at least one surfactant.

9. The method according to claim 1, wherein the liquid composition or liquid fraction is separated using filtration, centrifugal treatment, or a combination thereof.

10. The method according to claim 1, further comprising performing a re-adsorption in the mixing stage, at least a part of the enzyme attaching to the solid fraction of the mixture during the re-adsorption.

11. The method according to claim 1, further comprising diluting the plant based feed with liquid before the enzymatic hydrolysis stage.

12. The method according to claim 1, further comprising recovering the lignin fraction.

13. The method according to claim 1, wherein the starting material is a wood based material or a mixture comprising wood based material.

14. The method of claim 1, wherein the lignin fraction is configured to be used as a source material in a hydrolysis, polymerization process, depolymerization process, degradation process, chemical treatment, manufacture of a composite material, lignin composite, activated carbon, carbon fiber, binder material, polymers, resins, phenolic component, dispersion agent or absorbent material, manufacture of feed, manufacture of food, combustion process, or any combination thereof.

15. The method of claim 1, wherein the liquid fraction is configured to be used as a source material in a fermentation, hydrolysis, chemical treatment, catalytic treatment, polymerization process, depolymerization process, degradation process, enzymatic treatment, manufacture of binder, manufacture of feed, manufacture of food, or any combination thereof.

* * * * *

UNITED STATES PATENT AND TRADEMARK OFFICE
CERTIFICATE OF CORRECTION

| | |
|---|---|
| PATENT NO. | : 11,230,691 B2 |
| APPLICATION NO. | : 16/340481 |
| DATED | : January 25, 2022 |
| INVENTOR(S) | : Sami Turunen et al. |

It is certified that error appears in the above-identified patent and that said Letters Patent is hereby corrected as shown below:

In the Claims

At Column 21, Lines 48-51 (Claim 3, Lines 1-4), please delete "the additive for preventing an enzyme adsorption is added to the plant based material, to a pre-mixing stage, or to any combination thereof." and insert --the additive for preventing an enzyme adsorption is added to the plant based material, to a pre-mixing stage, to the enzymatic hydrolysis stage, or to any combination thereof.-- therefor.

Signed and Sealed this
Sixteenth Day of May, 2023

Katherine Kelly Vidal
*Director of the United States Patent and Trademark Office*